United States Patent [19]

Ciaudelli

[11] 4,026,818

[45] May 31, 1977

[54] TRANSPARENT RINGING GELS

[75] Inventor: Joseph P. Ciaudelli, Ramsey, N.J.

[73] Assignee: Van Dyk & Company, Incorporated, Belleville, N.J.

[22] Filed: Dec. 19, 1975

[21] Appl. No.: 642,558

[52] U.S. Cl. .............................. 252/316; 252/356; 252/357; 424/172
[51] Int. Cl.² ..................................... B01J 13/00
[58] Field of Search .................... 252/316; 424/172

[56] References Cited

UNITED STATES PATENTS

| | | | |
|---|---|---|---|
| 2,259,466 | 10/1941 | Harris et al. | 252/316 X |
| 3,101,301 | 8/1963 | Siegal et al. | 252/316 X |
| 3,175,949 | 3/1965 | Siegal | 252/316 X |
| 3,341,465 | 9/1967 | Kaufman et al. | 252/316 |
| 3,507,806 | 4/1970 | Barker et al. | 252/316 |

*Primary Examiner*—Richard D. Lovering

[57] ABSTRACT

Aqueous transparent ringing gel compositions are prepared utilizing (2-ethyl-1,3-dihydroxy)2-propyl oleamide, a Kritchevsky base, and isostearic acid as necessary components. Other cosmetic materials can be utilized as desired.

3 Claims, No Drawings

TRANSPARENT RINGING GELS

FIELD OF THE INVENTION

The concept of clear, ringing gels was developed a little over a decade ago and the consumer was immediately attracted. The initial consumer appeal for this product form generated a great deal of work in this area.

A gel can be defined as a mixture, one component of which is a fluid, homogeneous down to substantially colloidal dimensions, capable of resisting a finite shearing force. Thus a gel may contain a substantial portion of a fluid component but would have an extremely high viscosity. Transparency occurs when the droplets within the dispersed phase have diameters less than one-fourth the wavelength of light.

Transparent gels should be thermodynamically stable and due to the small particle size of the dispersed droplets, active ingredients in a gel may be absorbed more rapidly upon topical application.

The phenomenon of ringing is a result of the manner in which the dispersed droplets are entrapped within the network structure of a gel. It has been suggested that the network within a gel consists of a rod-like or lamellar structure. Such a network could allow dispersed particles to vibrate within a gel much like a ball bounces off the walls of a box.

DESCRIPTION OF THE PRIOR ART

Clear gels have been prepared using ethoxylated lanolin alcohols, polyethoxylated ethers of oleyl alcohol and their phosphate esters, carboxyl vinyl polymers, and polyethylene glycol esters of fatty acids such as lauric and oleic. These compounds alone or in combination with such cosmetic ingredients as alkylolamides, mineral oil, 2-ethyl-1, 3,hexanediol, polyethylene glycols, and various other polyhydric alcohols have been used to develop formulas for clear gels.

Clear gels prepared using ethoxylated lanolin alcohols required a high ratio of surfactant to mineral oil, e.g., 3:1, with low levels of water. These gels were tacky, defatting to the skin, sometimes irritating, and expensive to produce; see Balsam and Sagarin (second edition) "Cosmetics, Science and Technology," page 158–159.

A decrease in tackiness and defatting was accomplished by the use of polyethoxylated ethers of oleyl alcohol. Lower ratios of emulsifier to oil could be used making the gels less expensive. Polyethyoxylated compounds can deactivate preservatives necessary to protect an oil in water gel against micro-organisms. Furthermore, many of the gels exhibited poor stability.

SUMMARY OF THE INVENTION

It has now been found that aqueous transparent ringing gel compositions can be prepared utilizing (2 ethyl-1,3-dihydroxy) 2-propyl oleamide, a Kritchevsky type base and isostearic acid as the necessary components. When these ingredients are properly proportioned with mineral oil, water and a coupler such as propylene glycol, 2-ethyl-1,3-hexanediol and similar compounds a transparent ringing gel is obtained.

Particularly surprising in this invention is the specificity of (2-ethyl-1,3-dihydroxy)-2-propyl oleamide for the purpose. Thus, other amides such as linoleic, palmitic, isostearic, myristic, and lauric acids were prepared and were much less effective.

DISCUSSION OF PREFERRED EMBODIMENTS (2-ethyl-1,3-dihydroxy)2-propyl oleamide can be prepared by reacting 2-amino-2-ethyl-1,3 propanediol with the methyl ester of oleic acid (methyl oleate) using a basic catalyst such as sodium methoxide, sodium hydroxide or potassium hydroxide under a vacuum keeping the temperature below 100° C. The reaction is relatively fast with the removal of by-product methanol.

The Kritchevsky bases, from the condensation of one mole of a higher carboxylic acid with two moles of diethanolamine, are the well known bases from cosmetic chemistry, see e.g. U.S. Pat. No. 2,094,609, and Proceedings of Scientific Section of The Toilet Goods Association, Number 25, May 1956, pages 37–41. Coconut fatty acid diethanolamide and lauric acid diethanolamide are particularly useful but others are also effective.

Isostearic acid is a necessary component to obtain the desired product. Oleic acid can also be used but does not produce a gel as clear. Stearic acid also produces a clear gel but it is not stable over a long period of time. As regards suitable cosmetic mineral oils, see e.g. U.S. Pat. No. 3,175,949.

The components accordingly can be utilized in the ranges of about the following percentages based on the total gel composition.

| Component | Ranges (% by Weight) |
| --- | --- |
| (2-ethyl-1,3-dihydroxy) 2-propyl Oleamide | 5 – 9 |
| Kritchevsky Base | 6 – 8 |
| Isostearic Acid | 1 – 3.5 |
| 2-ethyl-1,3-hexanediol | .5 – 2.5 |
| Water | 60 – 70 |
| Mineral Oil | 12 – 16 |

Perfumes, color, antiseptic compounds and preservatives may be added in conventional small amounts without disturbing the gel characteristic of the basic composition of this invention.

Brightly colored transparent gels can be produced by using any water soluble dye available to the food industry. Combination of dyes can produce any desired color for a gel.

Preservatives such as methyl p-hydroxy benzoate, propyl p-hydroxy benzoate and benzyl-p-benzoate alone or in combination can be used to protect a gel from microbial attack. Other microbiocides can be used.

The following examples are representative of preferred embodiments of the invention and it will be understood that they are nonlimiting in nature and are only illustrative of some of the modes.

EXAMPLES I AND II

Formulations were prepared as follows:

| | | |
| --- | --- | --- |
| (2-ethyl-1,3-dihydroxy)2-propyl oleamide | 8.47 | 5.63 |
| Coconut fatty acid diethanolamide (2:1) (Foamole 2-AC) | 8.47 | 7.04 |
| Propylene Glycol | 0.85 | 0.70 |
| 2-Ethyl-1,3-Hexanediol | 0.85 | 0.70 |
| Isostearic Acid | 1.69 | 2.82 |
| Mineral Oil | 15.25 | 12.68 |
| Water | 64.42 | 70.43 |

Clear, stable ringing gels were thus obtained without the use of polyethoxylated compounds. The ratio of emulsifiers to mineral oil is approximately only 1:1 and a high percentage of water desirably was used to prepare the gels.

EXAMPLE III

| | |
|---|---|
| (2-ethyl-1,3-dihydroxy)2-propyl oleamide | 5.56 |
| Lauric Acid Diethanolamide (Ninol AA-62-Stepan Chemical Co.) | 6.35 |
| Isostearic Acid | 2.38 |
| Mineral Oil | 14.29 |
| Ethylene Glycol | 2.38 |
| 2-Ethyl-1,3-hexanediol | 1.59 |
| Water | 67.46 |

This example illustrates that other Kritchevsky bases can be utilized. Also, the ratio of emulsifier to mineral is less than 1:1. In addition, other polyols can be used to produce a clear gel.

The gels prepared in the examples have been found to be stable under conditions usually encountered in the manufacturing, storage and shipping. There was found to be little or no change in the pH of the gels under ambient, oven and refrigerator temperatures over a three-month period. There was no indications of the gels becoming hazy or liquifying with the passage of six months at room temperature.

In general, formulations of the (2-ethyl-1,3-dihydroxy) 2-propyl oleamide and isostearic acid are conveniently marketed to the trade, and are especially adapted for preparing the gels. If desired a Kritchevsky base can also be included.

The advantages for this invention will be apparent to the skilled in the art, e.g., the use of only amide type emulsifiers and no ethoxylated products to deactivate preservatives, lower ratio of surfactant to mineral oil, and a high percentage of water in the formula.

It will be understood that this invention is not limited to the specific examples which have been offered as specific embodiments and that modifications may be made without departing from the spirit thereof.

What is claimed is:

1. An aqueous, transparent ringing gel comprising

| Component | Ranges (% by Weight) |
|---|---|
| (2-ethyl-1,3-dihydroxy) 2-propyl Oleamide | 5 – 9 |
| Kritchevsky Base from the condensation of one mole of a higher carboxylic acid with two moles of diethanolamine | 6 – 8 |
| Isostearic Acid | 1 – 3.5 |
| 2-ethyl-1,3-hexanediol | .5 – 2.5 |
| Water | 60 – 70 |
| Mineral Oil | 12 – 16. |

2. An aqueous, transparent ringing gel comprising

| Component | Ranges (% by Weight) |
|---|---|
| (2-ethyl-1,3-dihydroxy) 2-propyl Oleamide | 5 – 9 |
| Coconut Fatty Acid Diethanolamide | 6 – 8 |
| Isostearic Acid | 1 – 3.5 |
| 2-ethyl-1,3-hexanediol | .5 – 2.5 |
| Water | 60 – 70 |
| Mineral Oil | 12 – 16. |

3. An aqueous, transparent ringing gel comprising

| Component | Ranges (% by Weight) |
|---|---|
| (2-ethyl-1,3-dihydroxy) 2-propyl Oleamide | 5 – 9 |
| Lauric Acid Diethanolamide | 6 – 8 |
| Isostearic Acid | 1 – 3.5 |
| 2-ethyl-1,3-hexanediol | .5 – 2.5 |
| Water | 60 – 70 |
| Mineral Oil | 12 – 16. |

* * * * *